United States Patent [19]

Stahl

[11] Patent Number: 5,665,079
[45] Date of Patent: *Sep. 9, 1997

[54] EYE DROP DISPENSER INCLUDING SLIDE

[76] Inventor: Norman O. Stahl, 3199 Monterey Dr., Merrick, N.Y. 11566

[*] Notice: The term of this patent shall not extend beyond the expiration date of Pat. No. 5,429,621.

[21] Appl. No.: 496,879

[22] Filed: Jun. 30, 1995

Related U.S. Application Data

[63] Continuation-in-part of Ser. No. 19,110, Feb. 18, 1993, Pat. No. 5,429,621.

[51] Int. Cl.⁶ .......... A61M 35/00; B65D 37/00; B65D 47/18
[52] U.S. Cl. .......... 604/298; 604/302; 222/219; 222/420; 222/421; 222/422
[58] Field of Search .......... 604/294–302; 222/214, 420, 421–422

[56] References Cited

U.S. PATENT DOCUMENTS

| Re. 28,873 | 6/1976 | Morgan. |
|---|---|---|
| 342,837 | 6/1886 | Olson. |
| 2,678,142 | 5/1954 | Creed. |
| 2,767,711 | 10/1956 | Ernst. |
| 2,783,923 | 5/1957 | Croce. |
| 2,920,624 | 1/1960 | Lerner et al.. |
| 3,279,466 | 10/1966 | Mings. |
| 3,439,674 | 4/1969 | Lelicoff. |
| 3,598,121 | 8/1971 | Lelicoff. |
| 4,022,168 | 5/1977 | Pettersen. |
| 4,043,331 | 8/1977 | Martin et al.. |
| 4,111,200 | 9/1978 | Sbarra et al.. |
| 4,134,403 | 1/1979 | Johnsen et al.. |
| 4,543,096 | 9/1985 | Keene. |
| 4,605,398 | 8/1986 | Herrick. |
| 4,846,637 | 7/1989 | Alderson et al.. |
| 4,946,452 | 8/1990 | Py. |
| 4,958,748 | 9/1990 | Otake. |
| 4,968,310 | 11/1990 | Menchel et al.. |
| 4,973,322 | 11/1990 | Jewart. |
| 5,064,420 | 11/1991 | Clarke et al.. |
| 5,069,675 | 12/1991 | Menchel et al.. |
| 5,137,178 | 8/1992 | Stokes. |
| 5,226,572 | 7/1993 | Gargione. |
| 5,366,448 | 11/1994 | Basilice. |
| 5,429,621 | 7/1995 | Stahl .......... 604/302 |

FOREIGN PATENT DOCUMENTS 474412 8/1969 Switzerland.

*Primary Examiner*—John G. Weiss
*Assistant Examiner*—Karin M. Reichle
*Attorney, Agent, or Firm*—Hoffmann & Baron

[57] ABSTRACT

A slide for an eye drop dispenser. The slide, which may be secured to a container, is formed with a longitudinally extending channel and a distal end configured to rest against the lower eyelid of an individual during administration of a drop to the eye. The dispensed drop rolls along the channel and into the eye.

30 Claims, 5 Drawing Sheets

EYE DROP DISPENSER INCLUDING SLIDE

The present application is a continuation-in-part of application Ser. No. 08/019,110 filed Feb. 18, 1993, now U.S. Pat. No. 5,429,621.

BACKGROUND OF THE INVENTION

The present invention relates to eye drop dispensers and, more particularly, to an eye drop dispenser employing a slide to assist in guiding a dispensed drop into the eye.

The use of eye drop dispensers is well known. Eye drops are employed for any number of reasons, from the elimination of "redness" caused by fatigue to the prevention of infection following surgery. These eye drops, whether of a prescription or over-the-counter nature, are typically packaged in a container having an eyedropper attached to its end. In order to administer the drop to the eye, a patient must tilt his or her head back, position the dropper over the eye and dispense the appropriate number of drops into the eye.

Although the procedure is easily described, many individuals find it difficult to self-administer eye drops. This finding is especially true with respect to the elderly, the invalid or those with vision problems. In particular, many patients find it difficult to properly position the dropper over the eye such that the dispensed drop will "fall" into the eye. Moreover, even assuming that the patient is able to properly position the dropper over the eye, the natural "blinking" reflex can result in the dispensed drop not entering the eye. This is both wasteful (in terms of dollars) and medically undesirable in that the patient may not be certain that the required dosage has been administered to the eye. Finally, many patients are uncomfortable with positioning an eyedropper, which typically includes an elongated tip, in close proximity to the eye for fear that the dropper will "poke" the exposed eye.

In addition, many eye drop dispensers include squeezeable containers or bottles having resilient walls which are compressed to administer one or more drops. Some bottles are more easily squeezed than others, and some persons experience difficulty in applying sufficient pressure to the walls to cause a drop to be dispensed.

Several prior art references disclose attempts to address drawbacks associated with conventional eye-droppers. For example, U.S. Pat. No. 4,968,310 (and related U.S. Pat. No. 5,069,678) discloses an applicator for liquid eye preparations. The applicator, although stated to ease the application of eye drops, is still hindered by the tendency of the patient to "blink" at the moment the drop is dispensed. Further, the design of the '310 applicator forces the patient to bring the elongated point of the applicator into close proximity with the eye, thereby increasing the likelihood of "poking" the eye or, at a minimum, increasing the fear of such happening.

Another prior art device is disclosed in U.S. Pat. No. 4,002,168. The '168 device is stated to be capable of dispensing a fluid into the eye without loss of such fluid due to inadvertent closing or blinking of the eye resulting from the fear of a sharp object being positioned proximal the eye. Still, the drop dispensed from the '168 device must fall into the eye, an occurrence that may cause blinking in and of itself. Finally, the '168 device employs an elaborately designed dispensing mechanism not readily adapted to the storage containers commonly used in the industry.

It would therefore be desirable to provide an eye drop dispensing assembly which facilitates the administration of eye drops by reducing the tendency of the patient to "blink" during administration of the drop and by also reducing the tendency of the user to "miss" the eye for fear of poking the elongated tip of the dropper into the eye. Such an assembly would allow a dispensed drop to "roll" into the eye, as opposed to having the dispensed drop "fall" into the eye. This eye drop dispensing assembly should also be inexpensive to manufacture and easily adaptable to the containers commonly employed in the industry.

SUMMARY OF THE INVENTION

The present invention, which addresses certain shortcomings of the prior art, provides an assembly for administering a drop of fluid to an eye of an individual. The assembly includes a container for storing fluid. The container includes means for dispensing a drop. In addition, the assembly includes a slide having a longitudinally extending channel for guiding drops dispensed from the dispensing means to the eye. The slide also has a distal end configured to rest against a lower eyelid of the individual during administration of the drop to the eye. Finally, the assembly includes means for securing the slide to the container.

The present invention additionally provides a method for administering a drop of fluid to an eye of an individual. The method includes the steps of providing an eye drop dispenser having a slide attached thereto. The slide includes a longitudinally extending channel for guiding drops dispensed from the eye drop dispenser to the eye and a distal end configured to rest against a lower eyelid of an individual. The method includes the additional step of positioning the distal end of the slide against the lower eyelid. Finally, the method includes the step of dispensing a drop of fluid from the container onto the slide such that the dispensed drop rolls down the channel and into the eye.

As a result, the present invention provides an assembly and method for facilitating the administration of eye drops by reducing the tendency of the patient to "blink" during administration of the drop. It also reduces the tendency of the user to "miss" the eye for fear of poking the elongated tip of the dropper into the eye. The present invention allows the dispensed drop to "roll" into the eye, as opposed to having the dispensed drop "fall" into the eye. Finally, the present invention may be easily manufactured and is easily adaptable for use with eye drop dispensers commonly employed in the industry.

DETAILED DESCRIPTION OF THE INVENTION

Figure 1:
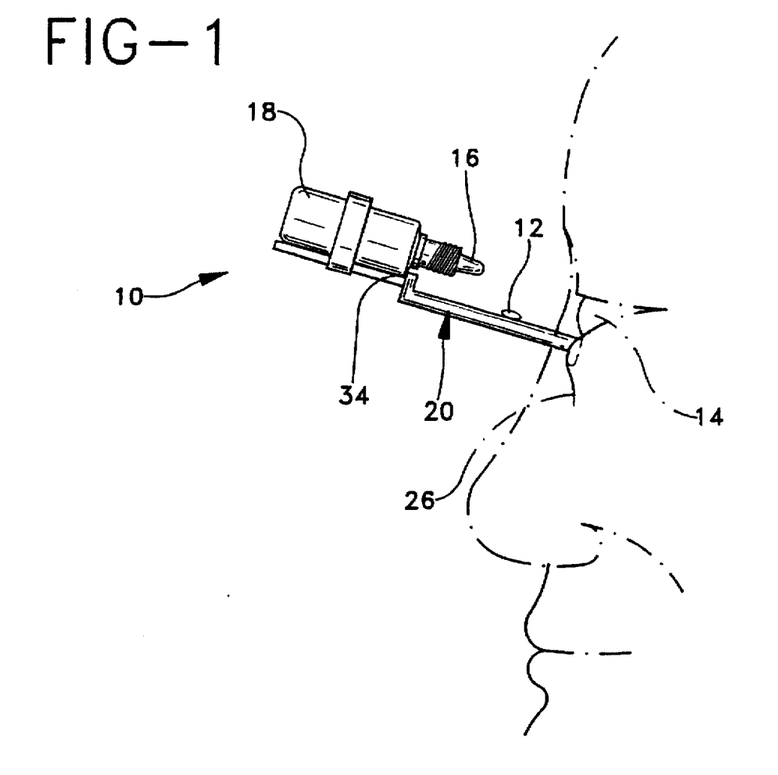
FIG. 1 is a side elevational view of the present invention during administration of a drop of fluid to the eye.

Referring to the drawings, FIG. 1 illustrates an assembly 10 being employed to administer a drop 12 of fluid to an individual's eye 14. The drop 12 is dispensed from an eyedropper 16 of a container 18, and is caused to roll down a slide 20 and into the eye. The container 18 preferably includes resilient walls which may be squeezed in order to dispense a drop. A cap (not shown) is threadably secured to the eyedropper when the container is not in use. The container is small enough to be easily held in one's hand.

Figure 1A:
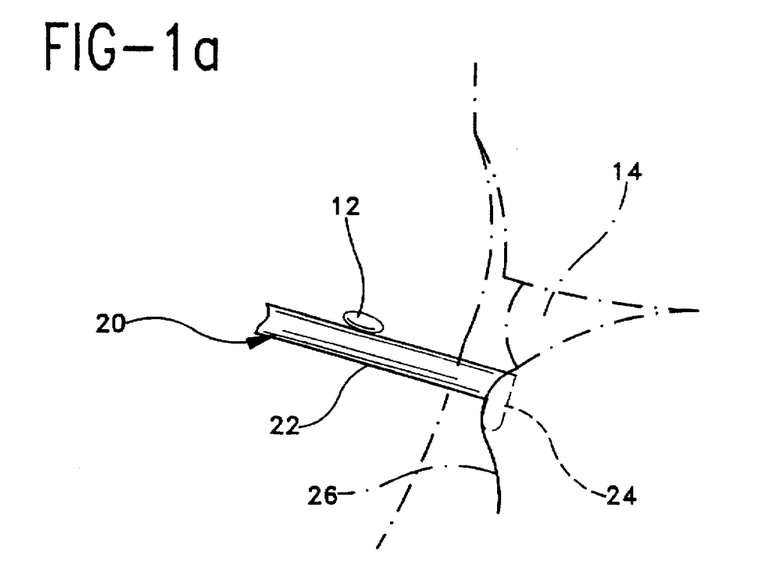
FIG. 1a is an enlarged detail of FIG. 1.
Figure 2:
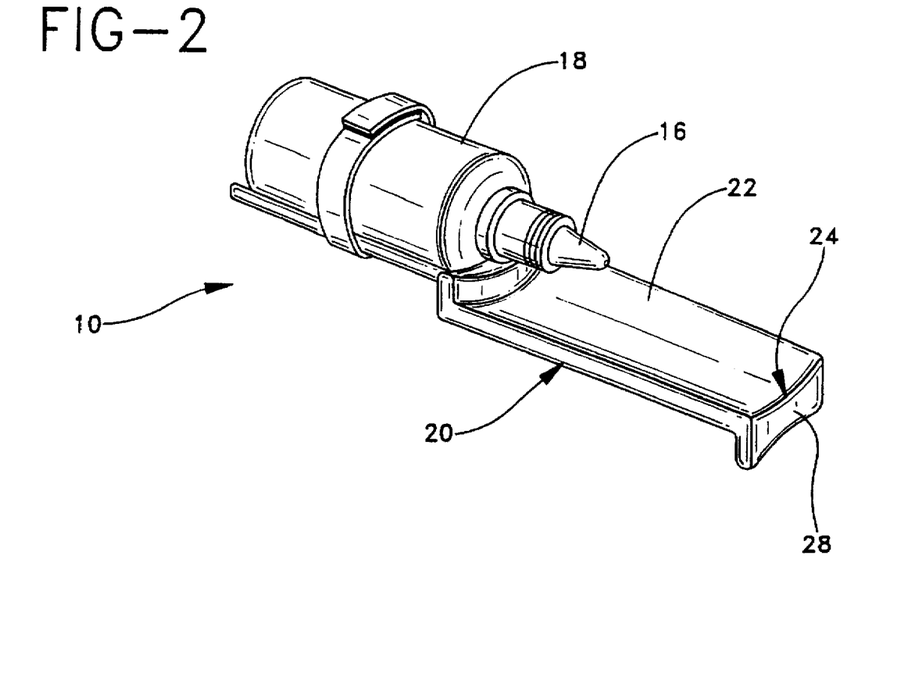
FIG. 2 is a perspective view of the present invention with a container secured thereto.

As best shown in FIGS. 1a–2, the slide 20 includes an elongated body 22 having a distal end 24 configured to rest against the lower eyelid 26 during administration of the drop of fluid to the eye. Preferably, the distal end 24 is rested against the inner wall of the eyelid. The slide 20 is preferably made of plastic.

Referring to FIG. 2, the distal end 24 of the slide 20 includes a gently curved flange 28 that extends downwardly from the body 22 of the slide. The flange provides a surface that may be rested against the upper or inner wall of the lower eyelid 26. In this regard, the flange has a bowed configuration including an outer surface that substantially conforms to the geometry of the eye socket.

The body portion 22 of the slide is also bowed. The upper surface thereof accordingly defines a longitudinally-extending channel which guides the drops towards the eye. The surface of the slide including the channel is preferably coated with a non-wetting material, e.g., "TEFLON" (polytetrafluoroethylene) or other such materials, in order to facilitate the rolling of the dispensed drop into the eye and to maintain sterility. It will be appreciated that the channel can be formed by providing a longitudinal groove in the slide which is aligned with the opening in the eyedropper 16. The channel is preferably bounded by side walls which converge in the direction of the distal end of the slide, as shown in the drawings.

Figure 3:
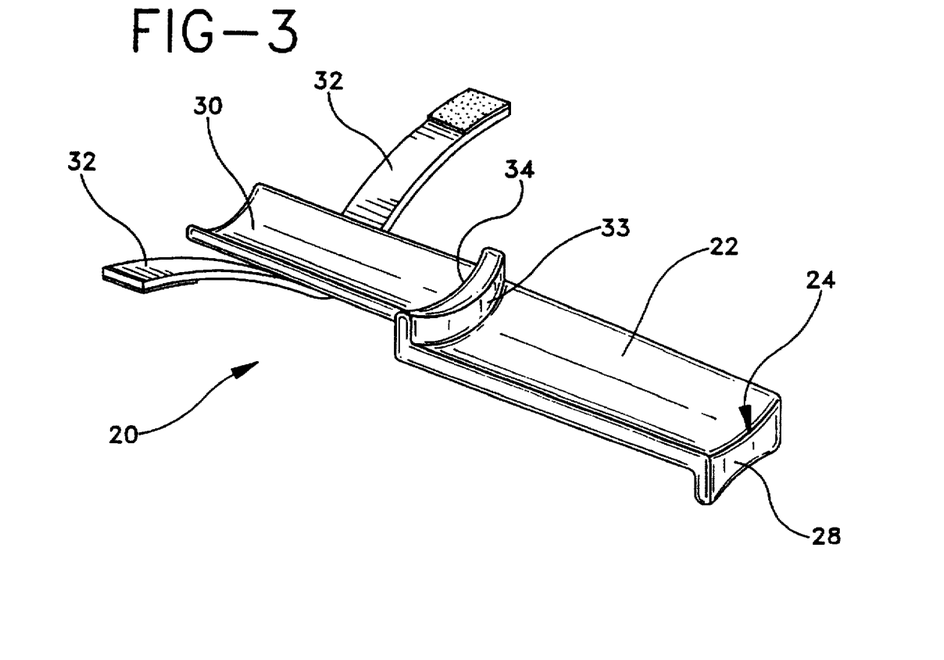
FIG. 3 is a perspective view of the present invention.

Referring to FIG. 3, a container-receiving track 30 is connected to the body 22 of the slide 20, and is preferably integral therewith. In particular, the track 30 is bowed, including a curved upper surface that is configured to substantially conform with the outer surface of the container 18. In this fashion, the container 18 may be laid on its side in the track 30 and, thereafter, secured in the track 30 by, for example, securing straps 32. Securing straps 32 may employ hook and loop type fasteners for closure. As also shown, a step 33 maybe integrated in the slide 20 between the track 30 and the body 22. The body 22 is accordingly in offset relationship with respect to the track 30 to facilitate the process of applying and removing the cap (not shown) onto the container 18 by providing additional radial space in the region surrounding the eyedropper 16. Additionally, a shoulder 34 (see FIG. 1) is formed at the junction of the track 30 and the body 22 to prevent the container from slipping towards the distal end.

As shown in FIGS. 2–3, the body 22 of the slide 20 is tapered in a direction towards the distal end 24. This configuration facilitates the process of administering a drop of fluid to the eye. The dispensed drop is thereby guided towards the center of the body 22 by the side walls of the channel as it travels towards the distal end 24 of the slide.

Figure 3A:
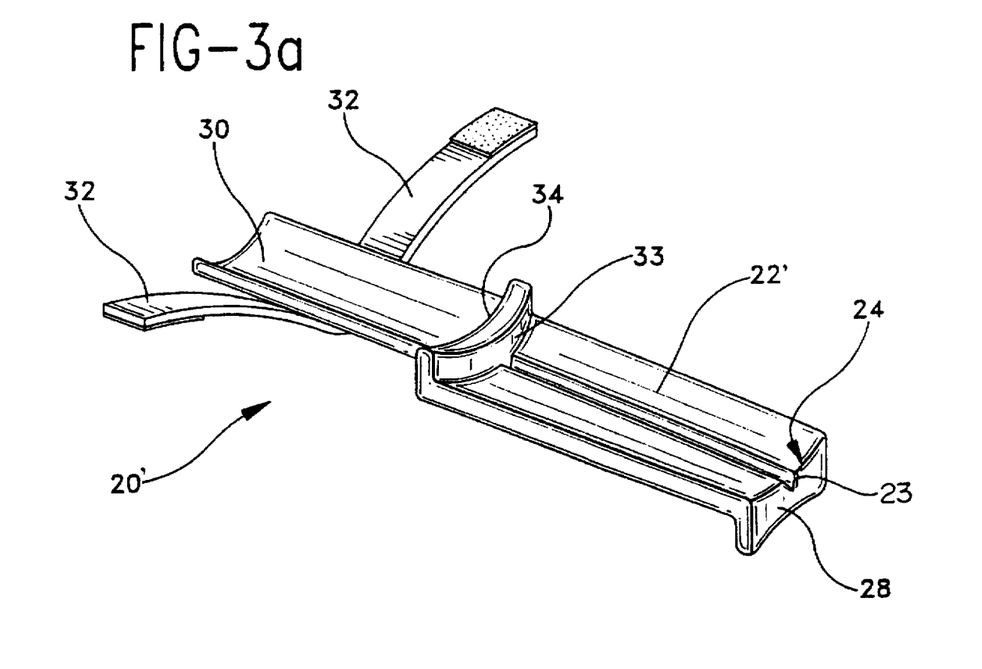
FIG. 3a is a perspective view similar to FIG. 3 showing an alternative embodiment having a longitudinally-extending V-shaped groove.

In an alternative embodiment, as shown in FIG. 3a, body 22' of slide 20' includes a longitudinally-extending V-shaped groove 23. The bowed side walls of body 22' therefore guide a dispensed drop of fluid into the V-shaped groove. The dispensed drop then travels along the groove towards the distal end of the slide and into the eye of the individual. Of course, groove 23 can be formed with other cross-sectional configurations including, among others, a U-shaped configuration.

Figure 4:
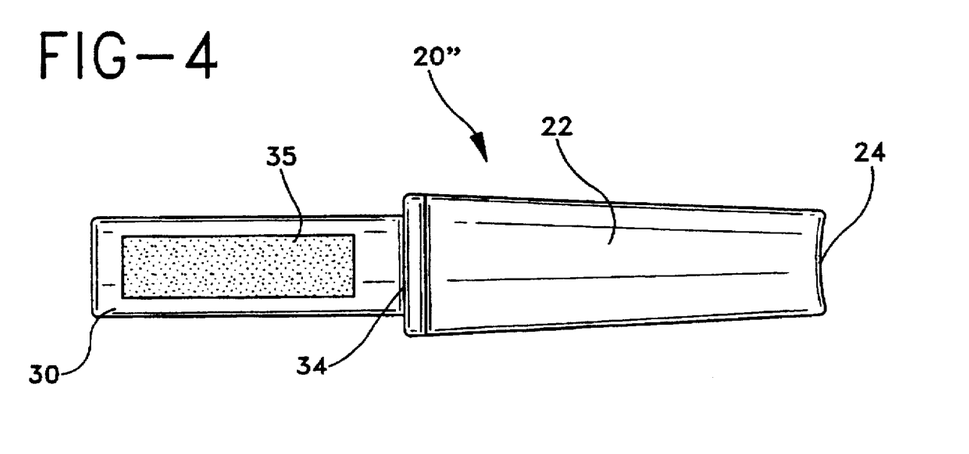
FIG. 4 is a top plan view of the present invention employing an alternative securing means.

FIG. 4 depicts an alternative and preferred means of securing the slide to the container. In particular, slide 20" includes a doubled-sided tape 35 secured to the track 30. To secure the slide to the container, the user merely removes a protective strip from the tape to expose a pressure-sensitive adhesive and presses the container onto the track. The tape adheres to the outside of the container and securely retains the container. Of course, other means of fastening the slide to the container may be employed, including a double-sided tape secured to the container rather than the slide.

Figure 5:
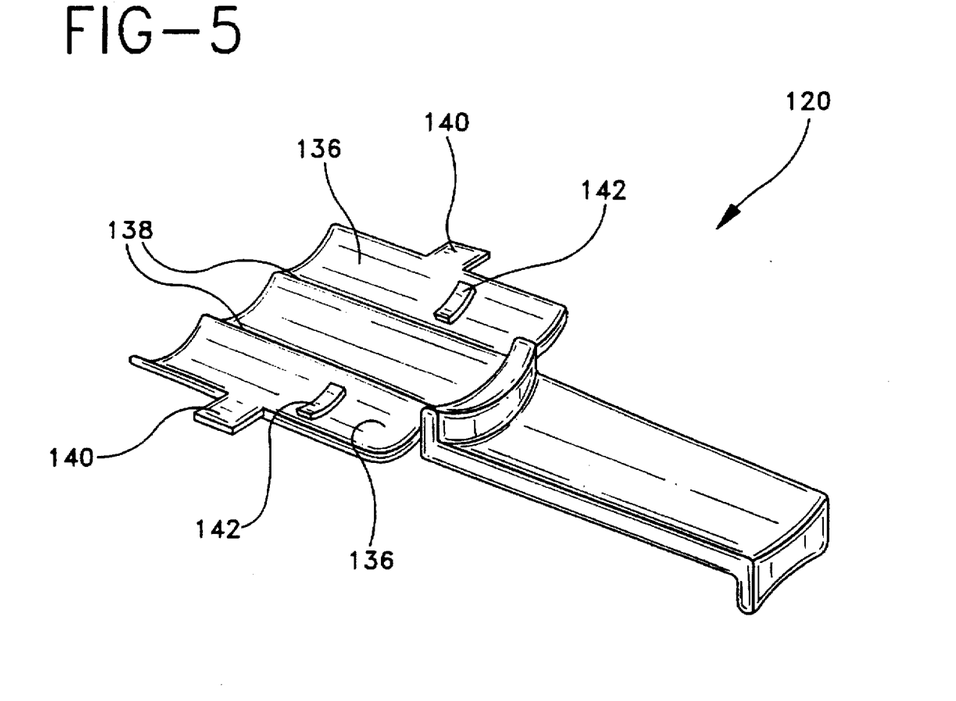
FIG. 5 is a perspective view of an alternative embodiment of the present invention.
Figure 6:
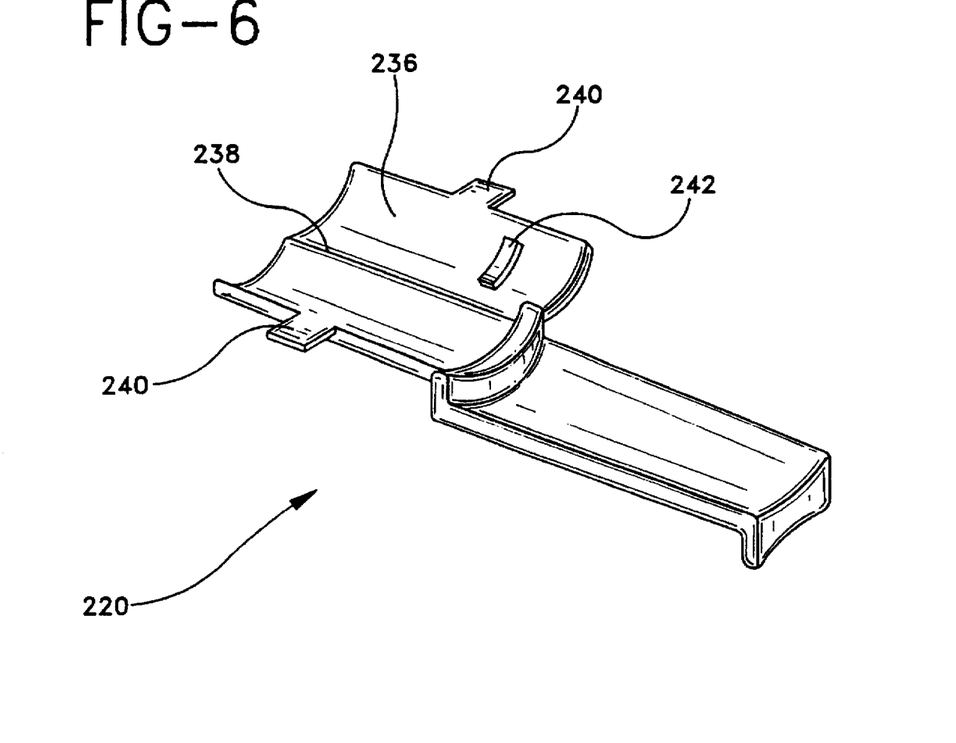
FIG. 6 is a perspective view of an another alternative embodiment of the present invention.

FIGS. 5 and 6 depict alternative embodiments of the present invention. Specifically, as shown in FIG. 5, the slide, i.e., slide 120, includes a pair of arcuate levers 136 pivotably attached to the track by living hinges 138. Attached to each lever is a finger tab 140. The levers 136 are configured to substantially surround the container when finger tabs 140 are squeezed together. Finally, an arcuate projection 142 is positioned in each of the levers to facilitate compression of the container.

Alternatively, as shown in FIG. 6, the slide, i.e., slide 220, includes a single arcuate lever 236 pivotably attached to the track by living hinge 238. The lever 236 is configured to substantially surround the container when finger tabs 240 are squeezed together. Because only a single arcuate lever is employed, one of the finger tabs 240 is attached directly to the track 230. Further, in this embodiment, only one projection 242 is employed.

The embodiments depicted in FIGS. 5 and 6 may also include means for regulating the amount of fluid which is dispensed therefrom. This may be accomplished by incorporating structure into the slide which limits the travel of the arcuate lever(s) when the finger tabs are squeezed together. As a result, the container will consistently only dispense a desired amount of fluid, for example, 1 to 1½ drops, per squeeze of the finger tabs.

Figure 5A:
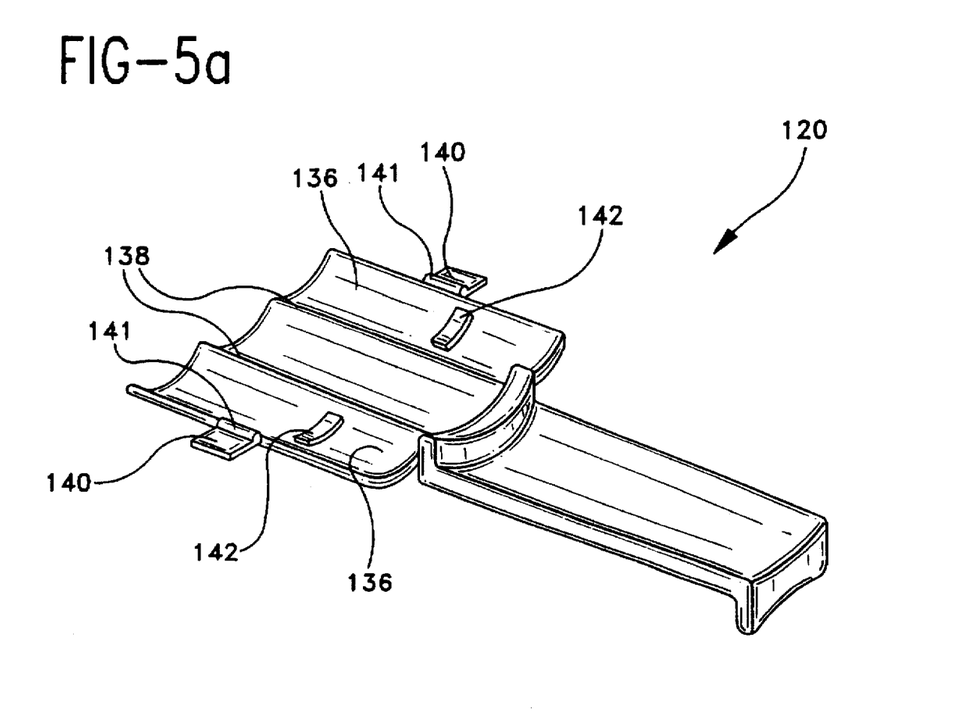
FIG. 5a is a perspective view similar to FIG. 5 showing an alternative embodiment which includes fixed travel limiting structure.

The structure for limiting the travel of the lever(s) may be fixed or adjustable. A dispenser having fixed travel limiting structure is shown in FIG. 5a (of course, such structure could also be incorporated into the slide of FIG. 6). The finger tabs include travel limiting ribs 141 which are dimensioned to contact one another when the finger tabs are squeezed. This limits the maximum compression of the container by the arcuate lever(s) to a predetermined amount, and thus regulates the amount to fluid dispensed therefrom. It is contemplated herein that the fixed travel limiting structure can include embodiments wherein only a single travel limiting rib is employed; wherein the configuration of the rib(s) is modified and/or wherein the rib(s) are disposed at alternative locations on the levers, as long as the structure limits the compression of the container to a predetermined amount upon squeezing of the finger tabs.

Figure 5B:
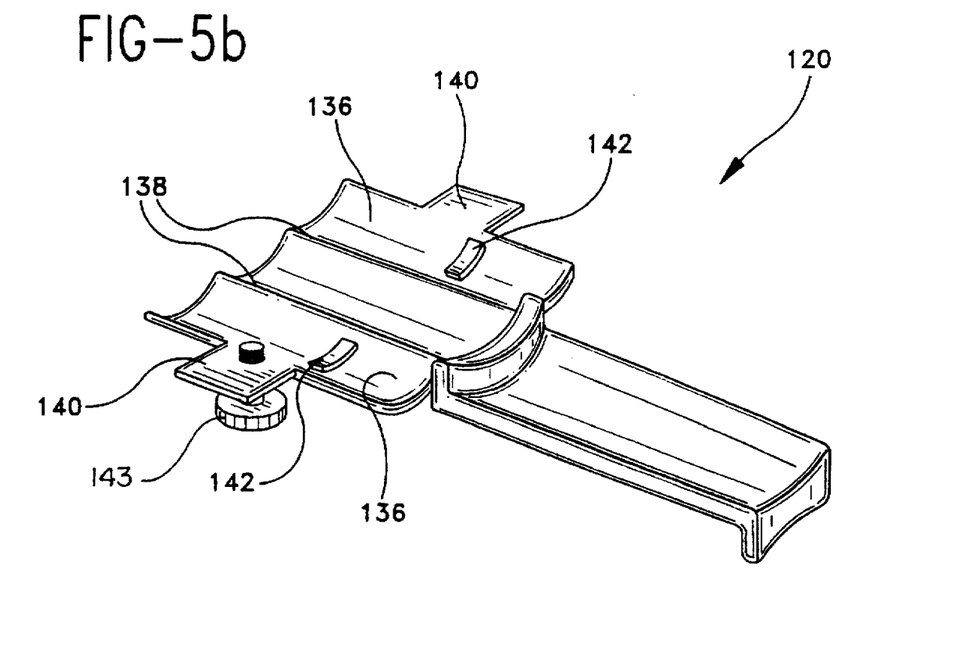
FIG. 5b is a perspective view similar to FIG. 5 showing an alternative embodiment which includes adjustable travel limiting structure.

A dispenser having adjustable travel limiting means is shown in FIG. 5b (again, this same structure could be incorporated into the slide of FIG. 6). This embodiment includes an adjustment screw 143 attached to one of the arcuate levers. When the finger tabs are squeezed together, the end of the adjustment screw will contact the surface of the opposing finger tab, and thus prevent further compression of the container. Turning the adjustment screw varies the amount of travel of the levers. This, in turn, regulates the amount of fluid dispensed from the container. Other arrangements which allow an individual to adjust the maximum compression of the container upon squeezing of the finger tabs are also contemplated.

To administer a drop of fluid to the eye, the user first secures the slide to the container if it has not already been secured. As discussed above, the straps or the double-sided tape may be employed for this purpose. The user then pulls the lower eyelid away from the eye and rests the distal end of the slide against such eyelid. Preferably, the user rests the distal end of the slide against the inner wall of the eyelid.

Because the distal end of the slide is configured to conform with the geometry of the eye socket, the user will be confident that he will not poke himself in the eye during administration of the drop. In addition, because the distal end is rested against the lower eyelid, that eyelid is less likely to close (i.e., blink) during administration of the drop. Moreover, the drop does not fall into the eye as commonly occurs in the prior art; instead, the drop is dispensed onto the body of the slide and, thereafter, gently rolls down the channel and into the eye. Finally, this administration process can be accomplished without the need for the user to tilt his or her head backward, a feat which can prove quite difficult for some people. Particularly, the user can maintain his or her head in a level position, pull the lower eyelid away from the eye, place the distal end of the slide against the inner wall of the lower eyelid, raise the other end of the slide (i.e., the end secured to the container), dispense a drop of fluid onto the body of the slide and allow such drop to roll into the eye.

With respect to the embodiment shown in FIGS. 5 and 6, the user, after positioning the slide, would squeeze together the finger tabs, thereby causing the lever(s) to engage the resilient walls of the container. Preferably, the lever(s) includes at least one projection positioned to press against the container when the lever is pivoted into engagement with the container. Such an arrangement facilitates the dispensing process for the elderly or invalid.

Specifically, with respect to the embodiment shown in FIG. 5, the levers may be urged upwards to surround the container. As the levers are pivoted about the hinges into engagement-with the container, e.g., by pressing together the finger tabs, the projection is pressed against the resilient walls of the container, whereby a drop of fluid is dispensed from the container. In similar fashion, the single lever employed with the embodiment of the FIG. 6 may be pivoted about its hinge into engagement with the container such that the arcuate lever substantially surrounds the container whereby the finger tabs may be squeezed together to dispense a drop of fluid-from the container. As already described, when the finger tabs are squeezed together, the projection is pressed against the resilient walls of the container and a drop of fluid is dispensed therefrom.

As discussed, the travel limiting structure shown in FIGS. 5a and 5b would limit the maximum compression of the container to a predetermined amount upon squeezing of the finger tabs. Thus, a known quantity of fluid, e.g., 1 to 1½ drops, is dispensed each time the tabs are squeezed.

When the container is empty, the user can remove the slide and dispose of the container. The slide can then be secured to and employed with a newly-purchased container of eye drops. It is preferred, however, that the slide is permanently attached to the container, in which case the entire assembly would be disposed of once the container is empty.

Thus, while there have been described what are presently believed to be the preferred embodiments of the invention, those skilled in the art will realize that various changes and modifications may be made to the invention without departing from the spirit of the invention, and it is intended to claim all such changes and modifications which fall within the scope of the invention.

What is claimed is:

1. An assembly for administering drops of fluid to an eye of an individual, comprising:

a container for storing fluid, said container including means for dispensing fluid in the form of drops;

a slide having a longitudinally-extending channel positioned directly under said dispensing means for directly receiving and transporting under the influence of gravity the dispensed drops to the eye, said channel terminating at a distal end which is gently curved to substantially conform to the geometry of an eye socket whereby said distal end may be safely rested against a lower portion of the eye to establish a continuous flow path from said channel to the eye during administration of the drops; and means for securing said slide to said container such that said dispensing means is portioned over said channel whereby the dispensed drops are directly received thereon.

2. The assembly according to claim 1, wherein said distal end includes a flange extending away from said channel in a direction substantially perpendicular thereto.

3. The assembly according to claim 1, wherein said slide includes a body portion defining side walls which converge in a direction towards said distal end to facilitate travel of the dispensed drops into the eye, said side walls bounding said channel.

4. The slide according to claim 1, wherein said channel includes a longitudinally-extending groove for receipt of the dispensed drops.

5. The assembly according to claim 1, wherein said channel is provided with a non-wetting surface.

6. The assembly according to claim 1, wherein said slide includes a body having a bowed configuration and a container-receiving track secured to said body, and wherein said body includes side walls converging in a direction towards said distal end to facilitate travel of the dispensed drops into the eye.

7. The assembly according to claim 6, wherein said body is offset with respect to said track to facilitate application and removal of a cap.

8. The assembly according to claim 6, wherein said slide includes means for preventing slippage of said container towards said distal end.

9. The assembly according to claim 6, wherein said means for securing includes an adhesive material, said track having an outer surface conforming to the outer surface of said container to facilitate securing said track to said container with said adhesive material.

10. A slide for administering drops of fluid from a container to an eye of an individual, comprising:

a body having a longitudinally-extending channel for directly receiving and transporting solely under the influence of gravity drops dispensed from an eyedropper of the container positioned directly thereover to the eye, said body terminating at a distal end which is gently curved to substantially conform to the geometry of an eye socket whereby said distal end may be safely rested against a lower eyelid of the individual to establish a continuous flow path from the channel to the eye during administration of the drops to the eye; and a container-receiving track secured to said body, said track including means for securing the container thereto.

11. The slide according to claim 10, wherein said distal end includes a flange extending away from said channel in a direction substantially perpendicular thereto.

12. The slide according to claim 10, wherein said body includes side walls converging in a direction towards said distal end to facilitate travel of said dispensed drop into said eye, said side walls bounding said channel.

13. The slide according to claim 10, wherein said body includes a longitudinally-extending groove to facilitate travel of the dispensed drops to the eye.

14. The slide according to claim 10, wherein said body is offset from said track to facilitate application and removal of a cap.

15. The slide according to claim 10, wherein said slide includes means for preventing slippage of the container towards said distal end.

16. The slide according to claim 10, wherein the container comprises resilient walls; and further comprising leverage means for selectively engaging the walls of the container whereby a drop of fluid is dispensable therefrom.

17. The slide according to claim 16, further comprising travel limiting structure which regulates the compression of the container to a predetermined amount whereby a select quantity of fluid is dispensable.

18. The slide according to claim 17, wherein said travel limiting structure comprises at least one fixed rib.

19. The slide according to claim 17, wherein said travel limiting structure comprise an adjustable screw which bears against a fixed surface of said slide upon actuation of said leverage means thereby regulating maximum compression of the container.

20. The slide according to claim 16, wherein said leverage means includes a projection, positioned to press against the container upon actuation thereof.

21. The slide according to claim 16, wherein said leverage means comprises an arcuate lever pivotably attached to said track.

22. The slide according to claim 21, further comprising a pair of finger tabs for squeezing said lever into engagement with the walls of the container; and wherein one of said tabs is connected to said lever and the other of said tabs is connected to said track opposite the location where said lever is pivotably connected to said track.

23. The slide according to claim 20, wherein said leverage means includes a pair of arcuate levers, the first of said levers pivotably attached to one side of said track, the second of said levers pivotably attached to another side of said track; and wherein each of said levers has a finger tab attached thereto for squeezing said levers into engagement with the walls of the container.

24. The slide according to claim 12, wherein said channel is provided with a non-wetting surface.

25. A method for administering a drop of fluid to an eye of an individual, comprising:

providing an eye drop dispenser having a slide attached thereto, said slide having a longitudinally extending channel directly positioned under said eye drop dispenser for directly receiving and transporting solely under the influence of gravity drops dispensed therefrom to said eye, said slide also having a distal end configured to rest against a lower eyelid of said individual;

positioning said distal end of said slide against said lower eyelid whereby a continuous flow path from said channel to the eye is established; and dispensing a drop of fluid from said eye drop dispenser such that the dispensed drop falls directly onto said slide and thereafter rolls solely under the influence of gravity along the channel and into the eye.

26. The method according to claim 25, wherein said distal end is rested against an inner wall of the lower eyelid.

27. The method according to claim 25, further comprising the step of maintaining a head of the individual in a substantially horizontal orientation.

28. The method according to claim 25, further comprising the step of positioning said eye drop dispenser at a higher altitude than said distal end so that the drop will roll towards said distal end and into the eye.

29. The method according to claim 25, wherein said eye drop dispenser comprises a container having resilient walls, and therein said slide includes leverage means for selectively engaging said walls of said container; and further comprising the step of causing said leverage means to deform said walls.

30. The method according to claim 25, wherein said eye drop dispenser comprises a container having resilient walls, and wherein said slide includes leverage means for selectively engaging said walls of said container, said slide further including travel limiting structure which limits compression of the container to a predetermined amount; and further comprising the step of causing said leverage means to deform said walls to said predetermined amount whereby a select quantity of fluid is dispensed.

* * * * *

UNITED STATES PATENT AND TRADEMARK OFFICE
CERTIFICATE OF CORRECTION

PATENT NO. : 5,665,079
DATED : September 9, 1997
INVENTOR(S) : Stahl

It is certified that error appears in the above-indentified patent and that said Letters Patent is hereby corrected as shown below:

In Claim 1, line 7,    "receiving and transporting under the influence" should be --receiving and transporting solely under the influence--;

In Claim 1, line 16,   "dispensing means is portioned" should be --dispensing means is positioned--; and In Claim 29, line 3,   "and therein said slide" should be --and wherein said slide--.

Signed and Sealed this

Eighteenth Day of November 1997

Attest:

BRUCE LEHMAN

Attesting Officer    Commissioner of Patents and Trademarks